US005658306A

United States Patent [19]

Kieturakis et al.

[11] Patent Number: 5,658,306
[45] Date of Patent: Aug. 19, 1997

[54] METHOD FOR MAKING ADDITIONAL INCISIONS IN LAPAROSCOPIC SURGERY

[75] Inventors: Maciej J. Kieturakis, San Carlos; James E. Jervis, Atherton; Kenneth H. Mollenauer, Santa Clara, all of Calif.

[73] Assignee: Archimedes Surgical, Inc., Menlo Park, Calif.

[21] Appl. No.: 269,559

[22] Filed: Jul. 1, 1994

[51] Int. Cl.$^6$ .................... A61B 17/34; A61M 5/00
[52] U.S. Cl. .................. 606/184; 128/898; 606/185; 604/164; 604/264; 604/49
[58] Field of Search .................... 604/164, 167, 604/171, 280, 264, 49, 53, 54; 606/184, 185, 167, 170; 128/898

[56] References Cited

U.S. PATENT DOCUMENTS

| | | |
|---|---|---|
| 2,945,496 | 7/1960 | Fosdal . |
| 3,920,001 | 11/1975 | Edwards ........................ 128/2 |
| 4,191,191 | 3/1980 | Auburn ........................ 128/347 |
| 4,431,426 | 2/1984 | Groshong et al. ................ 604/280 |
| 4,453,928 | 6/1984 | Steiger ........................ 604/53 |
| 4,535,773 | 8/1985 | Yoon ........................ 604/51 |
| 4,601,710 | 7/1986 | Moll ........................ 604/165 |
| 4,610,242 | 9/1986 | Santangelo et al. ................ 128/4 |
| 4,654,030 | 3/1987 | Moll et al. ................ 604/165 |
| 4,684,369 | 8/1987 | Wildemeersch ................ 604/272 |
| 4,762,519 | 8/1988 | Frimberger ................ 604/280 |
| 4,763,662 | 8/1988 | Yokoi ........................ 128/660 |
| 4,770,163 | 9/1988 | Ono et al. ................ 128/6 |
| 4,826,481 | 5/1989 | Sacks et al. ................ 604/54 |
| 4,836,205 | 6/1989 | Barrett ........................ 128/340 |
| 4,881,537 | 11/1989 | Henning ........................ 606/84 |
| 5,041,089 | 8/1991 | Mueller et al. ................ 604/96 |
| 5,116,353 | 5/1992 | Green ........................ 606/184 |
| 5,147,316 | 9/1992 | Castillenti ................ 604/164 |
| 5,147,376 | 9/1992 | Pianetti ........................ 606/170 |
| 5,152,749 | 10/1992 | Giesy et al. ................ 604/164 |
| 5,191,898 | 3/1993 | Millar ........................ 128/748 |
| 5,203,773 | 4/1993 | Green ........................ 604/104 |
| 5,209,736 | 5/1993 | Stephens et al. ................ 604/164 |
| 5,224,952 | 7/1993 | Deniega et al. ................ 606/184 |
| 5,226,426 | 7/1993 | Yoon ........................ 128/753 |
| 5,226,890 | 7/1993 | Ianniruberto et al. ................ 604/164 |
| 5,232,451 | 8/1993 | Freitas et al. ................ 606/174 |
| 5,256,149 | 10/1993 | Banik et al. ................ 604/164 |
| 5,258,003 | 11/1993 | Ciaglia et al. ................ 606/185 |
| 5,271,380 | 12/1993 | Riek et al. ................ 128/4 |
| 5,279,567 | 1/1994 | Ciaglia et al. ................ 604/117 |
| 5,292,310 | 3/1994 | Yoon ........................ 604/158 |
| 5,297,536 | 3/1994 | Wilk ........................ 128/4 |
| 5,312,357 | 5/1994 | Buijs et al. ................ 604/164 |
| 5,334,185 | 8/1994 | Giesy et al. ................ 604/164 |
| 5,336,237 | 8/1994 | Chin et al. ................ 606/167 |
| 5,336,252 | 8/1994 | Cohen ........................ 607/119 |
| 5,348,541 | 9/1994 | Lyell ........................ 604/164 |
| 5,395,030 | 3/1995 | Kuramoto et al. ................ 227/179 |

OTHER PUBLICATIONS

Jerry D. Giesy & Matthew W. Hoskins, Surgical Technology: Inside-Out Technique for Suprapubic Cystotomy: A New Device, Current Surgery, Aug. 1991, pp. 354–357.

Primary Examiner—Robert A. Hafer
Assistant Examiner—Benjamin Koo
Attorney, Agent, or Firm—Skjerven, Morrill, MacPherson, Franklin & Friel; Norman R. Klivans

[57] ABSTRACT

A method for locating additional cannulae in surgery on a patient having a body with tissue and overlying skin with the use of a guide member having proximal and distal extremities comprising introducing the distal extremity of the guide member through the skin of the body to a first location in the body. The distal extremity of the guide member is advanced in a direction below the skin to a second location remote from the first location. The distal extremity of the guide member is advanced through the skin of the patient at the second location from within the body to a position outside the body so that the distal extremity is exposed outside the body. A cannula is placed over the distal extremity of the guide member and is advanced through the skin of the patient at the second location utilizing the guide member as a guide. The distal extremity of the guide member is removed from the cannula.

19 Claims, 7 Drawing Sheets

METHOD FOR MAKING ADDITIONAL INCISIONS IN LAPAROSCOPIC SURGERY

In co-pending application, Ser. No. 08/124,283 filed Sep. 20, 1993 there is disclosed an apparatus and method for developing an anatomic space for a laparoscopic procedure. It has been found that in such laparoscopic procedures and other surgical procedures there are occasions which arise which make it difficult to guide cutting devices such as trocars from outside of the body to a precise location in the anatomic space within the body of the patient without at least on some occasions, causing undesired injuries to the body, as for example injury of an epigastric artery in hernia repair. There is therefore a need for a method and apparatus which makes it possible to readily achieve additional incisions needed in laparoscopic surgery through which cannulae may be introduced without causing undesired injuries to vessels and other anatomical structures with the body wall of the human body.

In general, it is an object of the present invention to provide a method and apparatus for making additional incisions in laparoscopic surgery and other types of surgery.

Another object of the invention is to provide a method and apparatus of the above character in which the additional incisions can be made with relative ease without causing undesired injury to vessels and other anatomic structures in the body.

Another object of the invention is to provide a method and apparatus of the above character in which a guide member, preferably tubular in shape, is utilized in an anatomic space to locate the region in which an additional incision is to be made from within the body.

Another object of the invention is to provide a method and apparatus in which a laparoscope can be utilized to view the progress of the guide member.

Another object of the invention is to provide a method and apparatus in which the guide member can be provided with a sharpened tip to permit penetration of the guide member through the skin of the patient from the inside of the body to the outside of the body.

Another object of the invention is to provide a method and apparatus of the above character in which the region of the skin overlying the area through which the guide is to be advanced is firmly held in position to facilitate penetration of the guide member through the skin.

Another object of the invention is to provide a method and apparatus of the above character in which a device is utilized by the surgeon to hold the skin of the patient in place while the penetration is being made by the guide member.

Another object of the invention is to provide a method and apparatus in which a scalpel can be used to assist making the penetration of the skin by the guide member.

Another object of the invention is to provide a method and apparatus of the above character in which the guide member is sized so that a cannula can be slid over the same and advanced through the additional incision into the anatomic space.

Another object of the invention is to provide a method and apparatus of the above character which can be readily incorporated into laparoscopic as well as other surgical procedures.

Another object of the invention is to provide an apparatus of the present invention which can be utilized with the method which is relatively inexpensive and which can be readily manufactured.

BRIEF DESCRIPTION OF THE DRAWINGS

Additional objects and features of the invention will appear from the following description in which the preferred embodiments of the invention are set forth in detail in conjunction with the accompanying drawings.

In general, the method of the present invention for locating additional cannulae in surgery on a patient having a body with tissue and overlying skin with the use of a guide member having proximal and distal extremities comprises introducing the distal extremity of the guide member through the skin of the patient in a first location so that it is in the body. The distal extremity of the guide member is then advanced below the skin of the body to a second location remote from the first location. Advancement of the distal extremity is continued through the skin of the patient at the second location from within the body to outside the body so that the distal extremity is exposed outside the body. A cannula is placed over the distal extremity of the guide member. The cannula is then advanced through the skin of the patient at the second location utilizing the guide member as a guide. The distal extremity of the guide member is then removed from the cannula.

More specifically, the apparatus 21 incorporating the present invention as shown in FIGS. 1–4 consists of a guide member 22 which is preferably tubular in shape and a conventional laparoscope 23 slidably and removably mounted in the guide member 22. The guide member 22 consists of a tubular member 26 with proximal and distal extremities 27 and 28. The tubular member 26 can be formed of a suitable material such as a medical grade plastic or alternatively of a metal such as aluminum or stainless steel. The tubular member 26 can be of a suitable diameter. Preferably it should be of a diameter which can slide through a standard 10–11 millimeter sleeve provided with a bore 31 extending therethrough which has a size so that it can readily accommodate a conventional laparoscope 23. The tubular member 26 should have a wall thickness to provide sufficient rigidity so that the tubular guide 22 can be pressed through the skin and tissue of a patient as hereinafter described. The tubular member 26 can be of various lengths. However, preferably for use on an adult human, it should have a length of 25–30 centimeters. The distal extremity is provided with a taper 32 of a suitable angle, as for example 30° with respect to the longitudinal axis of the tubular member 26. The tapered distal end 32 is also sharpened by providing an inwardly extending beveled edge 33 (see FIG. 3) so that the distal extremity has a knife-like penetrating edge to facilitate penetrating the skin and tissue of a patient as hereinafter described. The guide member 22 also includes a guide 36 that is provided with a base 37 secured to the outer surface of the guide member 26 by suitable means such as welding. The guide 36 is provided with an outwardly and proximally inclined intermediate portion 38 and an adjoining outer fork portion 39 which has a slot 41 therein opening proximally and used for a purpose hereinafter described. The guide member 22 also includes a handle 46 which is in the form of an oval-shaped ring 47 having a finger hole 48 therein facilitating grasping of the tubular guide 22 by a finger of the human hand as hereinafter described.

Figures 1, 2, 3, 4, 5, 6:
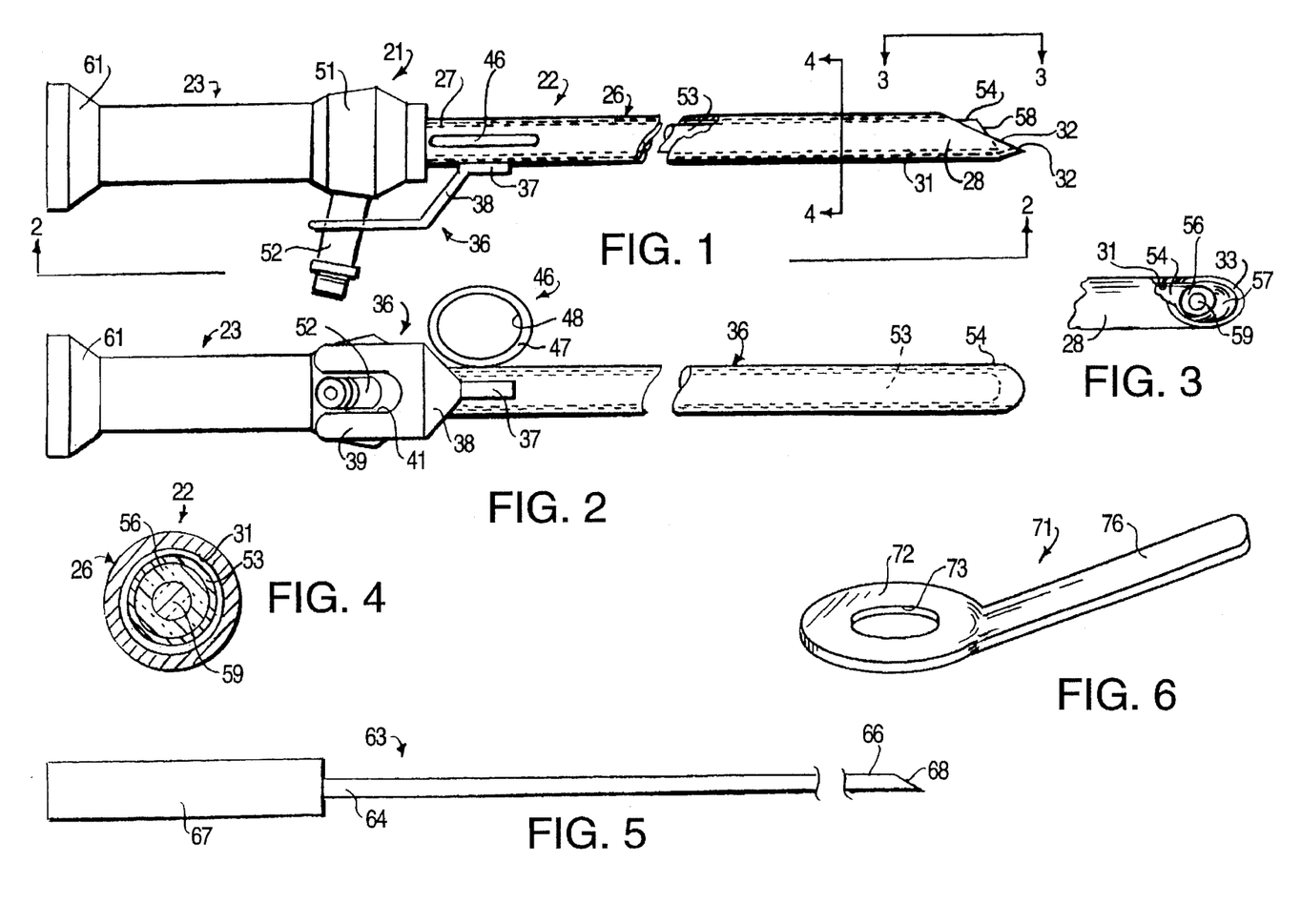
FIG. 1 is a side-elevational view partially in section of a guide member incorporating the present invention with a laparoscope disposed therein.
FIG. 2 is a side-elevational view of the guide member and laparoscope shown in FIG. 1 rotated by 90°.
FIG. 3 is a view partially in section of the distal extremity of the guide member shown in FIG. 1 looking along the line 3—3 of FIG. 1.
FIG. 4 is an enlarged cross-sectional view taken along the line 4—4 of FIG. 1.
FIG. 5 is a side elevational view of a stylet for use in the present invention.
FIG. 6 is an isometric view of a hold down device incorporating the present invention and adapted to be utilized in conjunction with the guide member shown in FIGS. 1 and 2.

As hereinbefore explained, the laparoscope 23 is of a conventional type and is provided with a body 51 having a fitting 52 extending radially and at an angle therefrom which is adapted to be connected to a conventional light source to supply light to the laparoscope to direct light through a cylindrical member 53 carried by the body 51 so that light is projected out of the distal extremity 54 of the cylindrical member 53 through an annular fiber bundle 56. The distal extremity 54 of such conventional laparoscopes typically permit viewing at a predetermined angle with respect to the longitudinal axis of the cylindrical member 53, as for example by looking straight ahead or alternatively by viewing at an angle, as for example of an angle of 30°.

The interior surface 57 of the tubular member 26 within the confines of the bevel 33 and beyond the distal extremity 54 of the cylindrical member 53 can have a non-reflective finish so as to minimize undesired reflections from the interior surface forming the bore 31 of the tubular member 26. As shown, the distal extremity 54 of the cylindrical member 53 can be provided with a suitable taper 58, as for example an angle of 30°. The images being viewed by the cylindrical member 53 are returned through a centrally located fiber optic 59 in the cylindrical member 53. An eye piece 61 is carried by the body 51 of the laparoscope 23 and is utilized to permit viewing of the advancement of the tubular guide 22 as hereinafter described.

As shown in FIGS. 1 and 2, the cylindrical member 53 has such a length so that the distal extremity 54 just protrudes beyond the proximal portion of the taper 32 and is proximal of the distal-most extremity of the taper 32 provided on the distal extremity 28 of the tubular guide 22. This ensures that the viewing capabilities of the laparoscope 23 are not impeded by the tubular guide 22 and that viewing can be accomplished at any desired angle from the longitudinal axis of the cylindrical member 53 as for example by 30 degrees. Reflections from the interior surface of the tubular guide 22 are minimized by utilizing a non-reflective surface such as by providing blackening on the interior surface 57.

The apparatus 21 includes a stylet 63 formed of a suitable material such as stainless steel and has proximal and distal extremities 64 and 66. A handle 67 is mounted on the proximal extremity 64. The distal extremity 66 is provided with a taper 68 to provide a knife-like cutting edge.

The apparatus 21 also includes a hold down device 71. The hold down device 71 shown in FIG. 6 is to be utilized with the guide member 22 as hereinafter described. The device 71 consists of a planar annular ring 72 of a suitable outside diameter such as 5 centimeters which is provided with a circular centrally disposed opening 73 of a suitable size, such as 2 centimeters. The opening 73 is sized so that the guide member 22 can readily extend therethrough as hereinafter described. A handle 76 of a size adapted to be grasped by the human hand, as for example one having a width of 1 inch and a length of approximately 4 inches is secured to the ring 72 and as shown can be formed integral therewith. The device 71 can be formed of a suitable material such as a medical grade plastic or a metal.

It should be appreciated that since the apparatus 21 of the prevent invention is relatively simple, the components thereof as for example the guide member and the hold down device 71 can be formed of relatively inexpensive materials such a medical grade plastic and disposed of after one use. Alternatively, if desired the guide member 22 and the hold down device 71 can be constructed of reusable materials as for example stainless steel and sterilized between laparoscopic or other surgical procedures.

Figure 7:
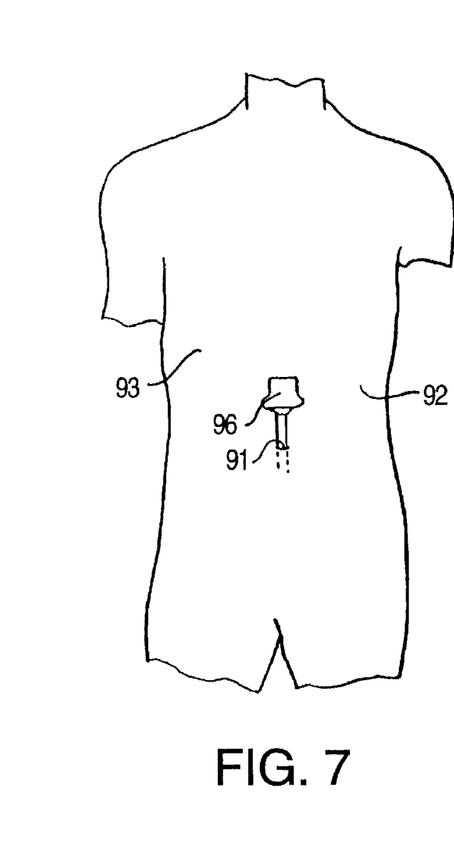
FIGS. 7–12 are cartoons showing the manner in which the method of the present invention is practiced utilizing the apparatus and devices shown in FIGS. 1–6.
Figure 8:
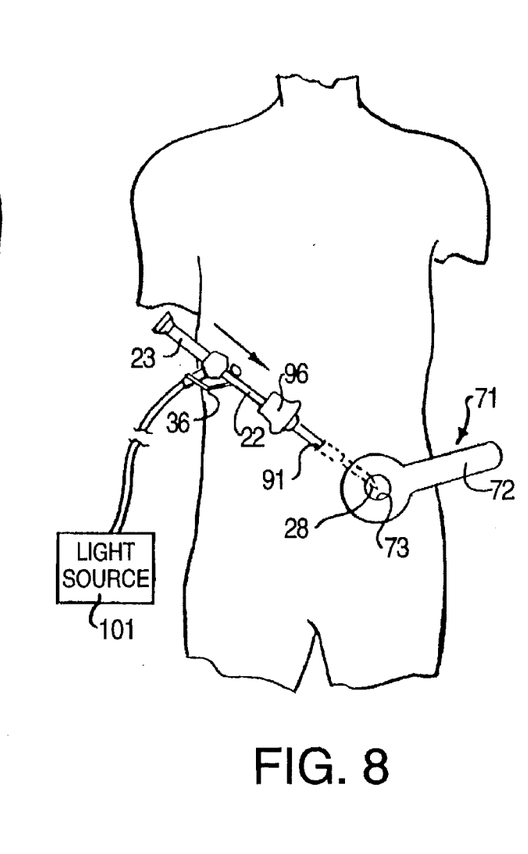

Operation and use of the apparatus shown in FIGS. 1–6 in performing the method of the present invention can now be briefly described as follows. In describing the procedure of the present invention let it be assumed that a laparoscopic surgical procedure such as that described in co-pending application, Ser. No. 08/124,283 filed on Sep. 20, 1993 is to be utilized in conjunction with the present invention. As described therein, let it be assumed that a hernia repair procedure is to be undertaken and that the surgeon has ascertained the appropriate fascia layer to be dissected. A first incision 91 can be made in the skin 92 of the body 93 of a patient (see FIG. 7) at the umbilicus or slightly lateral of the umbilicus. As soon as the rectus muscles that run longitudinally of the body of the patient on both sides of the umbilicus or navel have been located, a balloon dissection apparatus of the type described in said co-pending application is introduced into the incision and extends longitudinally of the patient's body generally parallel to the two sets of the rectus muscles. Typically, the first incision can be said to be made in a first region or location on the patient's body with the desire to utilize the balloon dissection apparatus to cause separation of the tissue in the body underlying the skin. As described in said co-pending application, the balloon dissector can be utilized to pass over the transversalis fascia to the level of the symphysis pubis. Thereafter the balloon can be inflated to dissect tissue overlying the peritoneum to provide an extraperitoneal working or anatomic space between the transversalis fascia and the rectus muscles. As soon as the desired amount of dissection has been completed, the balloon of the balloon dissection apparatus can be deflated and thereafter removed through the incision leaving the trocar introducer or sleeve 96 (see FIG. 8) which typically is a part of the balloon dissection apparatus. The dissected space is then insufflated with a suitable gas, as for example carbon dioxide to provide the desired anatomic space to complete the surgical procedure.

Thereafter rather than inserting standard trocars from outside of the body into the extraperitoneal working or anatomic space, the new method of the present invention is performed. This method is undertaken by taking the guide member 22 with the laparoscope 23 mounted therein and connected to a conventional light source 101. The combination of the guide member 22 with the laparoscope 23 therein is inserted through a trocar introducer or sleeve 96 into the extraperitoneal space underlying the incision 91. It should be appreciated, however, that if desired the guide member 22 can be inserted first into the trocar introducer 96 and thereafter the laparoscope 23 inserted into the guide member 22.

After the guide member 22 has been introduced into the extraperitoneal space or anatomic space in a first region underlying the first incision 91 and assuming that the next additional incision which is to be made into the skin 92 of the body 93 of the patient is to be at the patient's left side and inferiorly downward from the incision 91 to a second region overlying the anatomic space remote from the first region or location, the surgeon while viewing the extraperitoneal space through the laparoscope 23 guides the distal extremity of the guide member 22. The surgeon typically will select an area underlying the skin 92 of the patient in the second region or location within dissected extraperitoneal space which is spaced from the epigastric artery and which is spaced from the peritoneal edge to select an ideal location for the additional incision through which another cannula assembly is to be introduced. At the same time that the surgeon is viewing the extraperitoneal space through the laparoscope 23, the light which is being emitted from the distal extremity of the laparoscope 23 can be seen through the skin 92. The dissected tissue and the skin overlying the extraperitoneal space is translucent thereby permitting the surgeon and/or the surgeon's assistant to observe externally of the body 93 the advancement of the distal extremity of the guide member 22 in the extraperitoneal space. The surgeon can utilize the light spot in the skin of the patient for defining the location of the second incision which then can be made with a scalpel. A cannula can then be introduced into this second incision to enter the extraperitoneal space. The guide member 22 can then be repositioned to another location and the same procedure can be followed for introducing another cannula.

Figure 9:
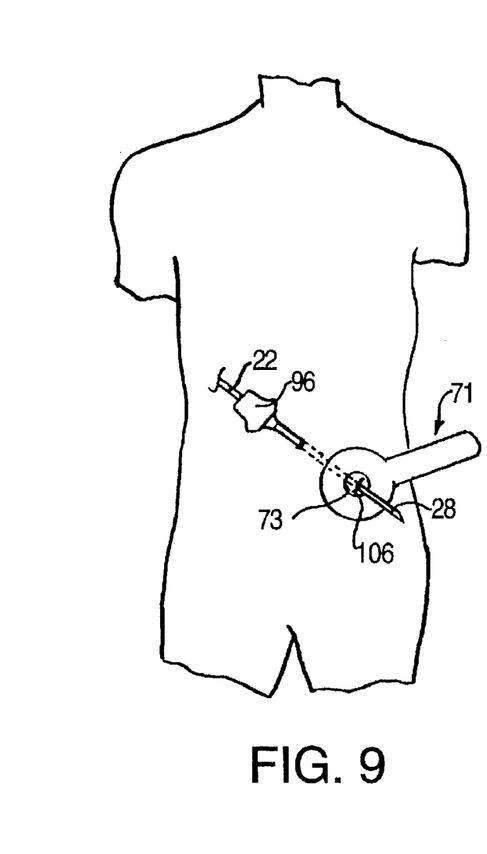
Figure 10:
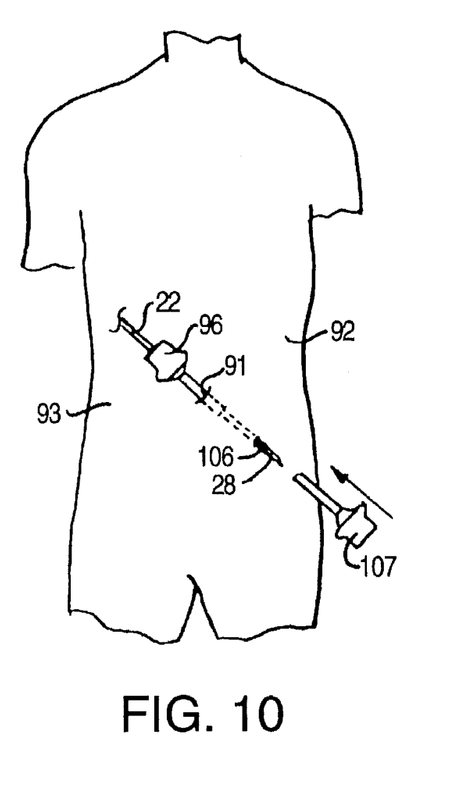

Alternatively, as soon as the distal extremity 28 of the guide member 22 has been advanced to the desired location in the second region or second location in the extraperitoneal space, the accessory hold down device 71 is taken and grasped by the handle 76 and positioned on the skin 92 of the patient in the region immediately overlying the second region or location where the additional cannula assembly is to be placed with the hole 73 therein to locate precisely the position in which the second incision is to be placed. While holding down the device 71 in one hand or by the hand of an assistant, the surgeon, with the other hand grasping the laparoscope 23 and the guide member 22, advances the sharp distal extremity 28 upwardly through the tissue and the skin 92 overlying the second region to cause a slight tenting of the skin to occur in this region. The tenting effect is minimized by pressing down on the hold down device 71 as shown in FIG. 9. Continued pushing on the distal extremity 28 of the guide 22 member by use of the laparoscope 23 as a handle causes the sharp knife-like distal extremity 28 of the guide member 22 to penetrate the skin 92 of the patient's body 93 from the inside out to form an additional incision 106 in registration with the hole 73 in the device 71 as shown in FIG. 10. In penetrating the skin 92, it may be desirable for the surgeon to rotate to some extent the guide member 22 to facilitate making the additional incision 106. Advancement of the tubular guide 22 is continued until a portion of the distal extremity 28 is exposed outside of the patient's body 93 as shown in FIG. 10.

It should be appreciated that this procedure can be accomplished without the use of the hold down device 71 because the surgeon could merely place his or her other hand over the region occupied by the hold down device 71 and push the distal extremity 28 of the tubular guide 22 through the skin from the inside out between the spread apart fingers of the surgeon's hand. This is undesirable because the knife-like sharpened distal end 28 may accidentally cut through the surgeon's latex glove and cut the surgeon's hand.

During the advancement of the guide member 22 with the laparoscope 23 therein, the surgeon can rotate the laparoscope 23 which by way of example as pointed out previously can have a viewing angle of 30 degrees from the longitudinal axis of the laparoscope to view the interior of the extraperitoneal space so that the surgeon can carefully view the advancement of the distal extremity of the guide member 22. The surgeon while accomplishing this rotation can mentally ascertain the rotational position of the distal extremity 28 by observing the positioning of the guide 36 carried by the proximal extremity of the guide member 22 which retains the rotational position of the laparoscope 23 in a predetermined angular rotation with respect to the guide member 22.

Thus, the surgeon by observing the position of the guide member 36 and by viewing the translucent spot appearing in the abdominal region of the patient can precisely ascertain the position of the distal extremity 28 of the guide member 22 to thereby greatly facilitate the surgeon's positioning of the distal extremity 28 of the guide member 22.

It should be appreciated that if desired, the distal extremity 28 of the guide member 22 can be provided with a relatively blunt extremity rather than the knife-like sharp distal extremity and still perform a procedure in accordance with the present invention. This can be accomplished by the surgeon cutting an additional incision (not shown) into the skin of the patient 92 with a scalpel (not shown) during the time that the distal extremity 28 is in that second region or location and then pushing the distal extremity 28 from the inside out through that additional incision (not shown) which would correspond to the additional incision 106 hereinbefore described. The distal extremity 28 would then still protrude externally through the additional incision which could be accomplished with or without the use of the hold down device 71.

Figure 11:
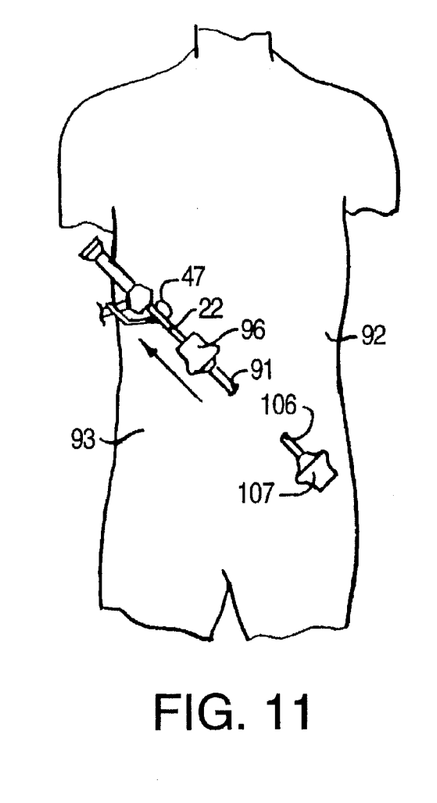
Figure 12:
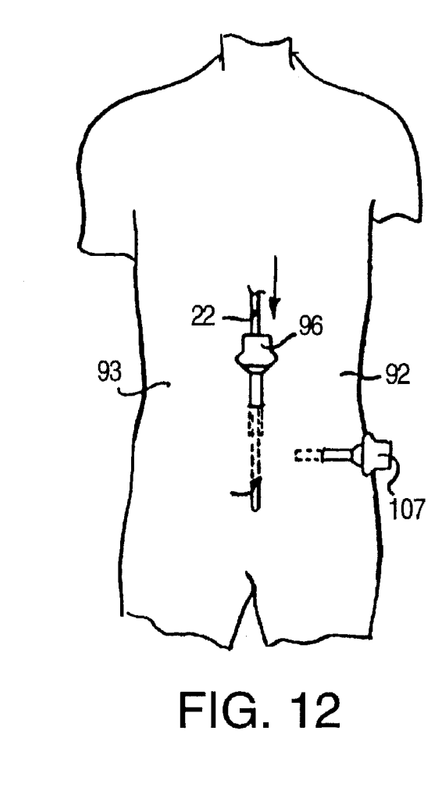

After the distal extremity of the guide member 22 has penetrated the skin 92 of the patient from the inside out with the distal extremity 28 exposed outside of the patient's body, the hold down 71 can be removed and an additional cannula assembly 107 can be placed over the distal extremity 28 of the guide member 22 using the guide member 22 as a guide which also can be characterized as a reverse guide or a reverse cannula as shown in FIG. 11. Thereafter, the additional trocar introducer or cannula 107 is pushed inwardly through the incision 106 into the extraperitoneal cavity in the second region of the patient's body as shown in FIG. 12. Thereafter, the guide member 22 with the laparoscope 23 is withdrawn sufficiently to clear the distal extremity of the additional cannula assembly 107 so that the distal extremity 28 is free to further navigate the extraperitoneal or anatomic space of the patient's body 93 if that is desired.

Alternatively, the distal extremity of the guide member 22 can be withdrawn from the second or additional incision after which the cannula can be inserted into the second or additional incision into the extraperitoneal space.

Assuming that it is desired to place another cannula in another or a third region within the extraperitoneal or anatomic space, the distal extremity 28 can then be repositioned as shown in FIG. 12 to again advance the distal extremity 28 of the guide member 22 into the extraperitoneal space. This also can be accomplished by observing advancement of the guide member 22 through the laparoscope 23 and at the same time observing the advancement of the translucent spot on the abdominal skin 92 on the outside of the patient's body. As soon as the desired location has been reached, the distal extremity 28 of the guide member 22 can be advanced through the abdominal skin 92 of the patient utilizing the hold down device 71 to cause the distal extremity to advance through the skin to form another incision 111 in the skin 92 of the patient. With the distal extremity 28 of the guide member 22 extending out of the body of the patient, another cannula assembly (not shown) can be placed over the distal extremity 28 and guided through the incision 111. The laparoscope 23 and the guide member 22 can then be removed from the trocar introducer 96 to permit completion of the laparoscopic procedure as described in co-pending application Ser. No. 08/124,283 filed on Sept. 20, 1993. In withdrawing the tubular guide 22 with the laparoscope 23 from the cannula assembly 107, the oval shaped handle 46 can be grasped by a finger engaging the finger hole 48 and pulling proximally the guide member 22.

In accordance with the hereinbefore described procedure utilizing the present invention, it has been assumed that the cannulae are of the same size as for example ones which can accommodate 10–11 millimeters devices being inserted therethrough. However, it should be appreciated that in laparoscopic procedures smaller trocar introducers or cannula assemblies can be utilized as for example a 5 millimeter size which is quite common in laparoscopic procedures. When a smaller size trocar is appropriate, a stylet 66 of the 5 millimeter size shown in FIG. 5 can be utilized and introduced through the cannula assembly 107 so that its distal extremity is advanced to a third location within the extraperitoneal or anatomic space while observing movement of the same through the laparoscope 23 carried by the guide member 22. Utilizing the same type of procedure, the distal extremity of the stylet 66 is pushed through by the hand of the surgeon grasping the handle 67 of the stylet 63 shown in FIG. 5 and pushing the distal extremity 68 from the inside to the outside through the hold down device 71. After the distal extremity is exposed, a 5 millimeter trocar introducer or sleeve can be placed over the distal extremity 68 and then pushed through the additional incision through the skin of the patient into the extraperitoneal space. The stylet 63 can be withdrawn and then if an additional cannula assembly is desired, it can be advanced to still another location under the viewing of the laparoscope 23 which can be moved to follow the path of the stylet 63 as it is being advanced. The stylet 63 can then be pushed from the inside out to make another incision through which a another cannula assembly can be placed through the skin in the same manner as hereinbefore described. After the desired number of trocar introducers or sleeves have been positioned in the extraperitoneal cavity or anatomic space, the guide member 22 with the laparoscope 23 therein can be removed and the laparoscopic procedure or other surgical procedure to be undertaken can be performed and completed.

Although the present invention has been described in connection with a hernia repair surgical procedure, it should be appreciated that the apparatus and method of the present invention can be utilized in other laparoscopic surgical procedures and other surgical procedures. For example, the method and apparatus of the present invention can be utilized with other laparoscopic procedures in which the peritoneum is penetrated and procedures are performed within the abdominal cavity. The same techniques can be utilized for locating additional locations through which cannula assemblies are to be positioned and to extend into the abdominal cavity. In this way, it is possible to precisely position the cannula assemblies without endangering anatomic vessels and structures within the abdominal cavity because the penetrations in the abdominal wall are from the inside out rather than from the outside in as with the use of conventional trocars. It also should be appreciated that the present invention can be utilized with surgical procedures other than laparoscopic procedures and still utilize the benefits of making penetrations through the abdominal wall from the inside to the outside in the manner hereinbefore described. Also it should be appreciated that in connection with the present invention, it has been found desirable to utilize a laparoscope in conjunction with the use of the guide member. However, in certain applications it may be unnecessary to use a laparoscope and in that case a solid guide member can be utilized.

Figure 13:
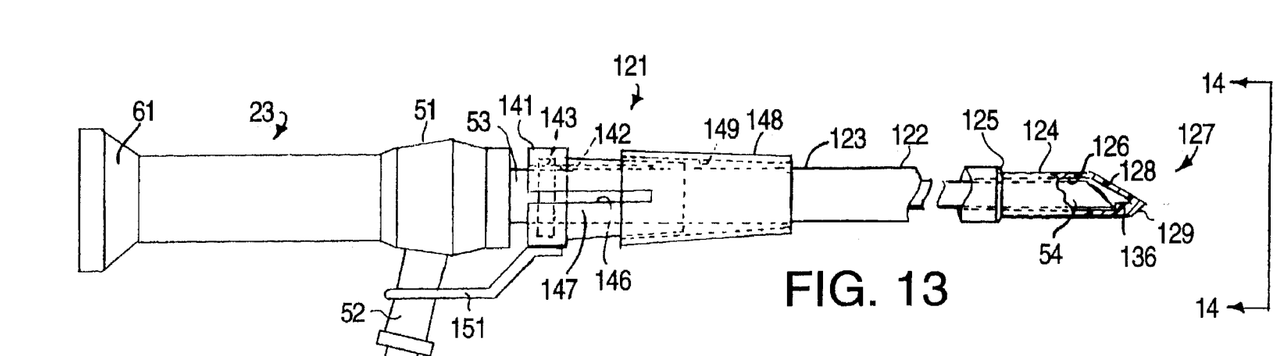
FIG. 13 is a side elevational view partially in section of a guide member incorporating another embodiment of the present invention with a laparoscope disposed therein.
Figure 14:
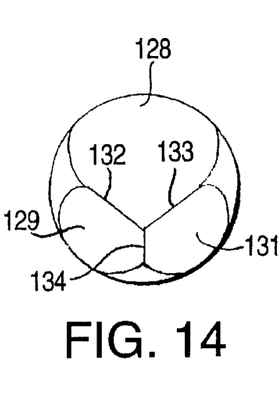
FIG. 14 is an enlarged end elevational view looking along the line 14—14 of FIG. 13.
Figure 15:
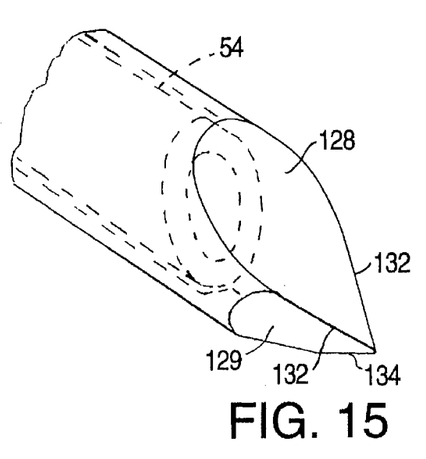
FIG. 15 is an isometric view of the distal extremity of the tubular guide shown in FIGS. 13 and 14.

Another apparatus 121 incorporating the present invention is shown in FIGS. 13–15. As shown therein, this apparatus consists of a guide member 122 tubular in form having proximal and distal extremities 123 and 124 and with a bore 126 extending from the proximal extremity 123 to the distal extremity 124. The distal extremity 124 is of reduced diameter and extends from a shoulder 125. The bore 126 at the distal extremity 124 is closed and is provided with a sharp pointed end 127 that is formed by three planar flats 128, 129 and 131 formed as shown in FIGS. 13, 14 and 15, in which flat 128 is a larger flat through which viewing is to occur and two smaller flats 129 and 131 which adjoin the flat 128 are to provide sharp, knife-like cutting edges 132, 133 and 134 between the flats 128, 129 and 131. The guide member 122 exhibits a distal extremity 124, which from the pointed tip has an increasing transverse cross-section in the proximal direction. The tip or end 127 has a sharp tip with incising cutting edges 132, 133 and 134 extending proximally therefrom, with the flats 128, 129 and 131 forming elliptical planar faces extending therebetween. Proximal of the knife-like cutting edges 132, 133 and 134, the tip 127 exhibits tissue displacing surfaces which are smoothly contoured to displace or push aside tissue without further incising the skin or underlying tissue.

An abutment 136 is provided within the interior of the bore and is formed integral with the guide member 122 and is adapted to be engaged by the distal extremity 54 of the laparoscope 23. The guide member 122 can be formed of a transparent material or, alternatively, the distal extremity of the guide member 122 can be formed of a transparent material to permit viewing through the closed end of the guide member by the laparoscope 23.

Means is provided for releasably securing the laparoscope 23 in a desired longitudinal position within the guide member 122 and also for retaining the laparoscope in a desired angular position with respect to the guide member 122. Thus, the proximal extremity 123 of the guide member 122 is provided with a cylindrical collar 141 which is formed integral therewith and which is provided with an internal annular recess 142 that carries a compressible seal ring 143 formed of a suitable material such as rubber. The proximal extremity 123 of the guide member 122 is provided with a plurality, as for example four circumferentially spaced-apart longitudinally extending slits 146 to provide slightly outwardly flared arcuate finger portions 147. A collar 148 is provided which is slidable axially on the guide member 122. The collar 148 is provided with a tapered bore extending therethrough which is adapted to receive and engage the outwardly flared finger portions 147. When the collar 148 is moved proximally toward the collar 141, it will create inward compressive forces to be applied to the finger portions 147 to cause the compressive ring 143 to be moved into frictional engagement with the cylindrical member or probe 53 of the laparoscope 23 to retain the laparoscope 23 in a desired longitudinal position within the guide member 122. In addition, a forked guide 151 of the type hereinbefore described is mounted on the collar 141 and extends over the fitting 52 to retain rotational registration of the laparoscope 53 with respect to the guide member 122.

Operation and use of the apparatus 121 is very similar to that hereinbefore described for the other embodiments and can be utilized in the same manner for forming incisions from the inside out as hereinbefore described. When a surgeon pushes the end 127 from the inside out of an anatomic space, an incision is made in the tissue underlying the skin which has a transverse dimension that is substantially less than the maximum transverse dimension of the guide member 122. After the initial incision takes place, the end 127 stretches the tissue and the overlying skin around the incision and presses the tissue outwardly from the guide member 122 until the maximum diameter of the guide member 122 has been reached. The smaller incision made in this manner facilitates rapid healing of the skin and underlying tissue.

After the distal extremity 124 of the guide member 122 penetrates the skin and is followed by the shoulder 125 so that an intermediate portion of the guide member 122 extends through the incision, a cannula assembly of the type hereinbefore described can be placed over the distal extremity 124 and seated against the shoulder 125. The spacing from the shoulder 125 to the end 127 is less than the length of the cannula assembly so that the sharp tip 127 will not damage the valve typically provided in such a cannula assembly. The shoulder 125 makes it easy for the cannula assembly to penetrate the incision as the guide member 122 is withdrawn from the incision because typically the cannula assembly has a wall thickness less than the width of the shoulder.

Viewing of the entire procedure being performed by the apparatus shown in FIG. 13 can be accomplished by viewing through the laparoscope 23 as the guide member 122 is advanced. Viewing is not substantially impaired through the transparent end 127. In the embodiment of the invention shown in FIG. 13, the laparoscope 23 has a viewing angle of approximately 30° so that viewing can be accomplished through the large elliptical planar face 128.

Figure 16:
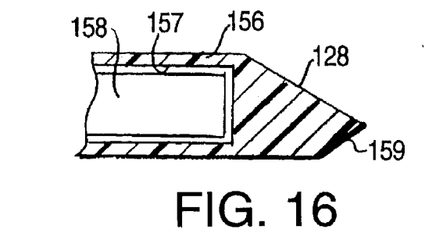
FIG. 16 is a partial side elevational view partially in section of the distal extremity of another embodiment of a guide member incorporating another embodiment of the present invention with a laparoscope mounted therein.

If it is desired to utilize a laparoscopic apparatus having the capability of viewing straight-ahead rather than at an angle, a guide member 156 such as shown in FIG. 16 can be utilized which is provided with a bore 157 having a laparoscope 158 therein. However, in this case, in order to accommodate the laparoscope 158, the bore 157 terminates at a right angle with respect to the wall of the guide member 156 forming the bore 157. However, in order to retain the incising capabilities of the tip 127 in the guide member 122 hereinbefore described, a tip 159 having the same external surfaces and configuration as that shown in FIG. 13 can be utilized with the principal difference being that the tip 159 is formed as a solid transparent material so as to permit viewing through the same by the laparoscope 158. Thus, it can be seen that such a guide member 156 can be utilized in the same manner as the guide member 122 in forming incisions from the inside out of an anatomic space.

Figure 16A:
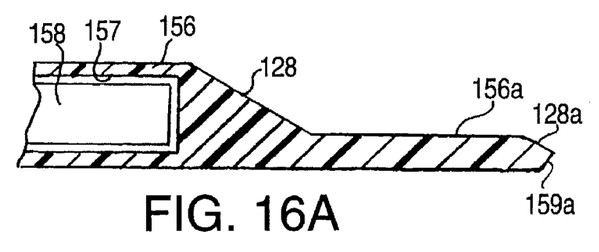

An alternative embodiment for the guide member 156 shown in FIG. 16 is shown in FIG. 16A in which the 10–11 millimeter guide member 156 is provided with an extension 156a of a smaller diameter such as 5 millimeters of a length ranging from 1 to 1.5 inches and having slots 128c and 129a formed thereon. This smaller diameter extension 156a makes it possible to use the guide member 156 shown in FIG. 16A for making incisions from the inside out for smaller 5 millimeter cannulae, as hereinbefore described.

Figure 17:
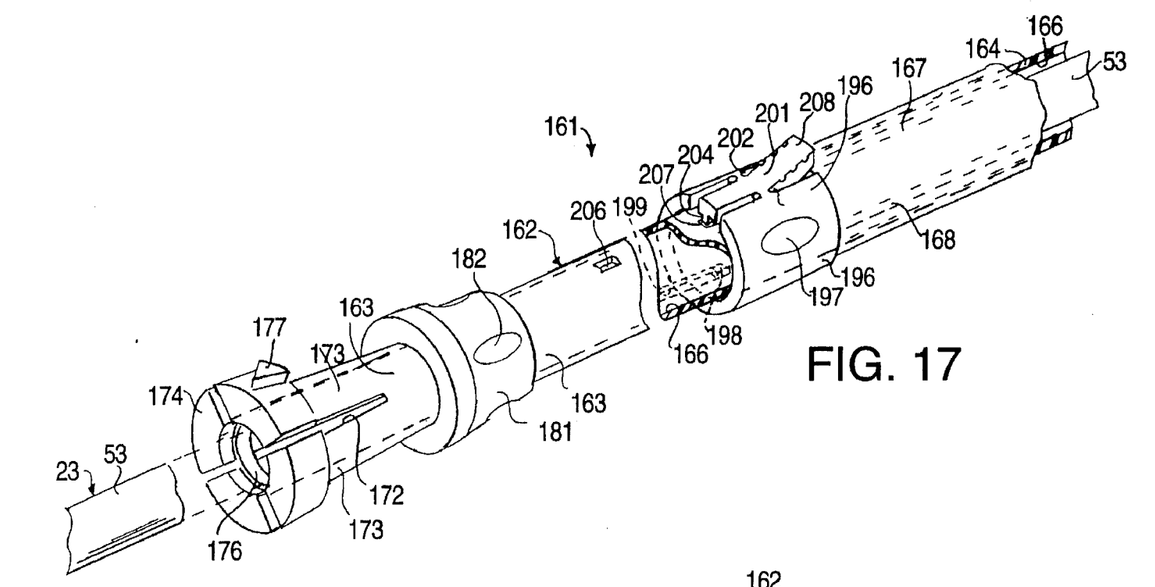
FIG. 17 is a partial isometric view of a guide member assembly incorporating another embodiment of the invention with a laparoscope mounted therein with the guide member being disposed in a non-cutting or non-incising position.
Figure 18:
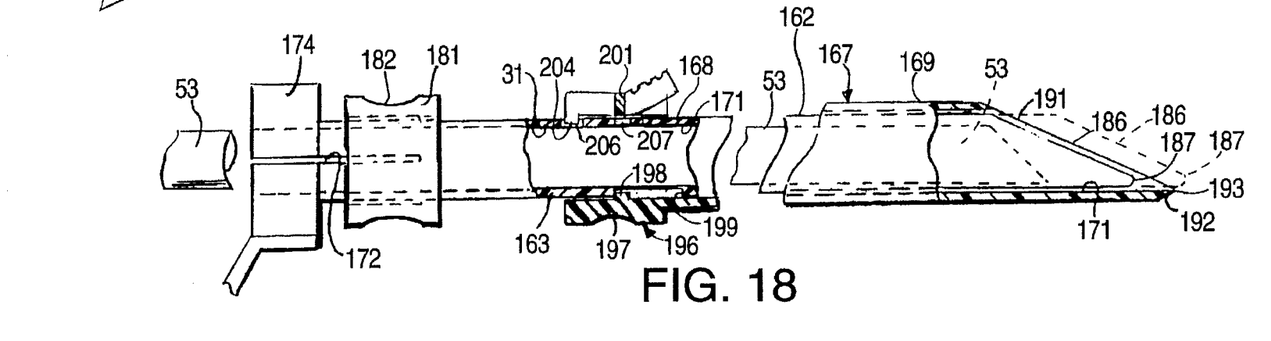
FIG. 18 is a side elevational view partially in section of the guide member assembly shown in FIG. 17.

Still another embodiment of a guide member assembly 161 incorporating the present invention is shown in FIGS. 17 and 18. The guide member assembly 161 consists of a first or inner guide member 162 which has proximal and distal extremities 163 and 164 with a bore 166 extending therethrough. The guide member assembly 161 also consists of a second or outer guide member 167 having proximal and distal extremities 168 and 169 with a bore 171 extending therethrough. The inner guide member 162 can be formed of a suitable material such as plastic, whereas the outer guide member 167 also can be formed of plastic or, alternatively, can be formed of a metal such as stainless steel. As can be seen, the inner member 162 is telescopically mounted within the outer guide member 167. The proximal extremity 163 of the inner guide member 162 is provided with circumferentially spaced-apart, longitudinally extending slots 172 to provide outwardly flared finger portions 173 which have collar portions 174 mounted on the proximal extremities thereof. A compressible washer 176 is mounted on the collar portions 174. A triangularly-shaped indicator 177 is carried by the collar 174 so as to provide a visual indication of the axial rotation of the inner guide member 162.

A cylindrical collar 181 having outwardly facing circumferentially spaced apart elliptical recesses 182 therein is slidably mounted on the proximal extremity 163 of the inner guide member 162 and is adapted to be moved proximally of the proximal extremity 163 to cause the compression washer 176 to frictionally engage the cylindrical member 53 of the laparoscope 23 to retain it in a desired longitudinal position within the guide member assembly 161.

The distal extremity 164 of the inner guide member 162 is provided with a tapered end 186 which is provided with a rounded distal-most portion 187. The distal extremity 169 of the outer guide member 167 is also provided with a tapered end 191 with a bevel 192 formed thereon to provide a sharp incising edge 193 capable of incising tissue.

Means is provided for causing relative telescoping movement between the inner guide member 162 and the outer guide member 167 and consists of a collar 196 formed integral with the proximal extremity 168 of the outer guide member 167. Circumferentially spaced apart outwardly facing elliptical recesses 197 are provided in the outer surface of the collar 196. The collar 196 is provided with a radially inwardly extending protrusion 198 which is adapted to travel in an elongate slot 199 provided in the inner guide member 162 (see FIG. 17) to retain the collar 196 in the desired angular orientation with respect to the inner guide member 162. Means is provided for latching the outer guide member 167 in one of two positions longitudinally with respect to the inner guide member 162 and consists of a hinged latch member 201. The hinged latch member 201 as shown in FIG. 17 can be formed integral with the collar 196 by the use of spaced-apart hinge portions 202. The latch member 201 is provided with a depending latch portion 204 which is normally urged inwardly in a radial direction so that it is adapted to engage either one of first and second longitudinally spaced apart notches 206 and 207 provided in the inner guide member 162. The latch member 201 is provided with a serrated portion 208 adapted to be grasped by the finger of a hand and to facilitate moving the latch portion 204 out of engagement with the notches 206 and 207 to permit the collar 196 to be slid axially along the outer guide member 167 relative to the inner guide member 162. Thus, when the latch portion 204 is disposed in the proximal-most notch 206, the sharper cutting edge 193 carried by the outer guide member 167 is retracted as shown in dotted lines in FIG. 18 so that the rounded blunt extremity 187 extends beyond the cutting edge to prevent the cutting edge 193 from being effective. Conversely, when the latch portion 204 is disposed in the distal-most notch 207, the guide member 167 will be advanced so that the sharp cutting edge 193 extends beyond the rounded tip 187 so that the sharp cutting edge 193 is exposed as shown in solid lines in FIG. 18 for incising operations of the type hereinbefore described.

Thus, it can be seen that the outer guide member 167 is concentrically and slidably mounted on the inner guide member 162, which when in the first position with the latch portion 204 in engagement with the notch 206, the distal extremity of the guide member assembly 161 is blunt and is incapable of incising tissue. In the second position, when the latch portion 204 is in engagement with the notch 207, the sharp edge 193 is advanced beyond the rounded blunt end 187 so that the guide member assembly 161 is capable of incising tissue when it is desired to make a penetration from inside an anatomic space to outside the skin of the body of a patient.

Also, it should be appreciated that the inner guide member 162 can be biased distally as for example by a spring (not shown) such that when the blunt distal extremity 187 of the inner guide member 162 encounters the tissue, the blunt end 187 can be moved inwardly against the bearing force so that the sharp cutting edge 193 of the outer guide member 167 can automatically protrude and perform the necessary incisions.

Figure 19:
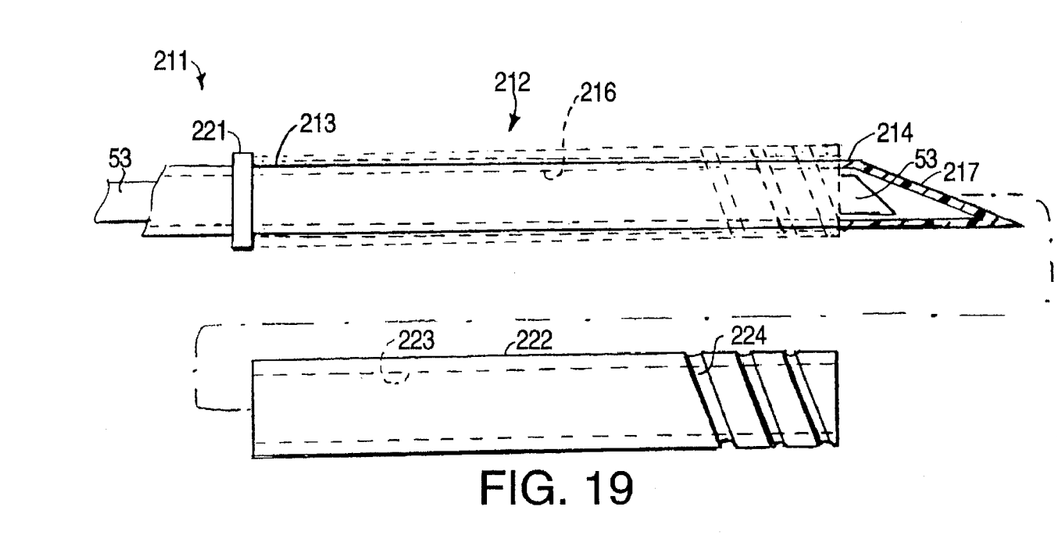
FIG. 19 is a partial side elevational view of another guide member assembly incorporating the present invention which includes a removable cannula.
Figure 20:
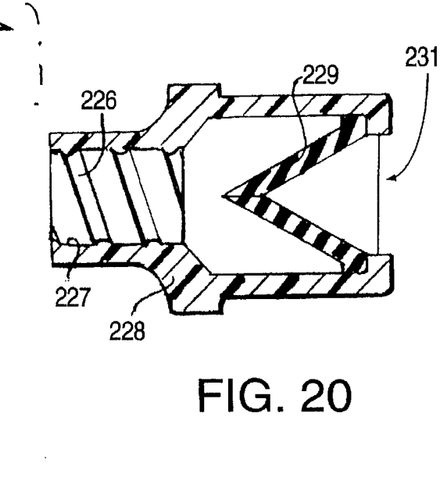
FIG. 20 is a cross-sectional view of a valve housing adapted to be threaded onto the removable cannula shown in FIG. 19.

Another apparatus 211 incorporating the present invention is shown in FIGS. 19 and 20. As shown therein, the apparatus 211 consists of a guide member 212 which is provided with proximal and distal extremities 213 and 214 and having a bore 216 extending therethrough. The distal extremity 214 is provided with a tapered end 217 which can be provided with incising edges of the type hereinbefore described. The bore 216 is sized to receive the laparoscope 23 so that the laparoscope can be inserted into the bore to permit viewing through the distal extremity 214 of the guide member 212. The distal extremity in accordance with the embodiments hereinbefore described can either be open or closed, as desired. A flange 221 is provided on the proximal extremity 213 of the guide member 212. The guide member 212 can be formed of a suitable material of the type hereinbefore described. For example, if the end is closed it can be formed of a transparent material. If the end 217 is open, it can be formed of a suitable material such as plastic or a metal.

The apparatus 211 also includes a cannula 222 which is provided with a bore 223 extending therethrough which is sized so that the guide member 212 can extend therethrough. The cannula 222 can be formed of a suitable material such as plastic or metal. Thus, as shown, the cannula 222 is adapted to be slid over and mounted on the guide member 212 as shown in dotted lines in FIG. 19. Cooperative mating means in the form of recessed threads 224 are provided on one end of the cannula 222. These recessed threads 224 are adapted to cooperatively mate with protruding threads 226 provided in the interior of a bore 227 of a valve housing 228 (see FIG. 20) which has a conventional duckbill valve 229 disposed therein which is accessible through a hole 231 provided in the housing 228. The housing 228 can be formed of a suitable material such as plastic.

In using the apparatus 211 in connection with the present invention, the cannula 222 is slid onto the guide member 212 until it is adjacent the flange 221. The guide member 212 can then be used in the manner hereinbefore described to probe an anatomic space and to find a location where it is desired to make an incision from inside the anatomic space to outside the body of the patient. The guide member 212 can be utilized to make an incision in the manner hereinbefore described and to carry with it the cannula 222 and to advance it through that incision so that the threads 224 extend outside the body. As soon as this occurs, the valve housing 228 can be taken and threaded onto the exposed portion of the cannula 222. Then by holding the housing 228 in one hand, the guide member 212 can be removed from the cannula 222 so that there remains in place a cannula assembly consisting of the cannula 222 and the housing 228. Thereafter, additional incisions can be made in a similar manner. The guide member 212 can be withdrawn and a new cannula 222 inserted thereon and then it can be introduced through the skin seal to make additional incisions from the inside out as desired.

Figures 21, 22, 24:
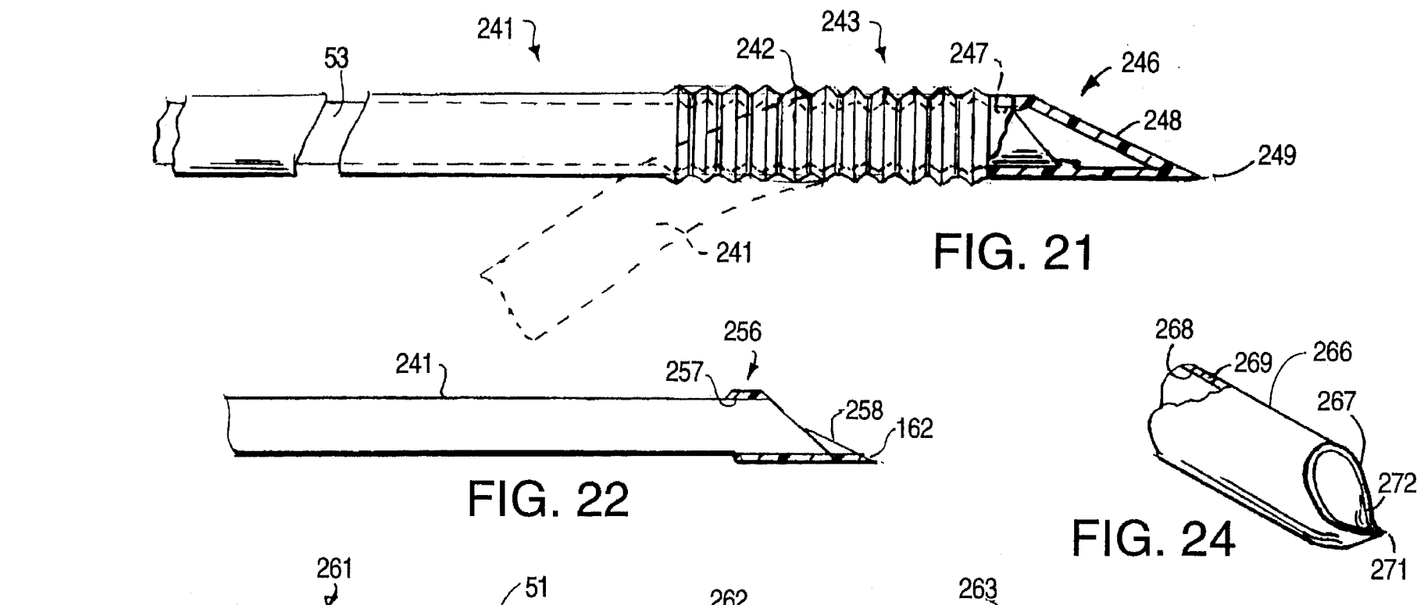
FIG. 21 is a side elevational view partially in cross section of the distal extremity of a guide member incorporating another embodiment of the present invention mounted on the distal extremity of a laparoscope.
FIG. 22 is a sectional view of a guide member incorporating another embodiment of the invention in the form of an attachment which has an open end for mounting on the distal extremity of a laparoscope.
FIG. 24 is an isometric view of the distal extremity of a guide member incorporating another embodiment of the present invention.

The method of the present invention also can be utilized with a steerable or articulating laparoscope 241 of a conventional type which is provided with a flexible distal extremity 242 having corrugations 243 permitting at least limited bending of the distal extremity as shown by dotted lines in FIG. 21. A guide member 246 is provided which can be formed of a suitable material such as a transparent plastic. It is provided with a cylindrical recess 247 formed to receive the distal extremity of the laparoscope 241 and secured thereto by suitable means such as an adhesive (not shown). When the guide member 246 is enclosed as shown, it is provided with a tapered surface 248 of the type hereinbefore described which can be provided with a knife-like incising edge 249. Such a laparoscope 241 can serve as a penetrating laparoscope and can be utilized for making incisions from the inside out from an anatomic space in the manner hereinbefore described for the previously disclosed guide members. After the distal extremity of the guide member 246 protrudes through the incision, a cannula assembly of the type hereinbefore described can be positioned over the guide member 246 and guided through the incision after which the distal extremity 242 of the laparoscope 241 can be removed carrying with it the guide member 246. After this has been accomplished, additional incisions from the inside out can be made by repositioning the distal extremity of the laparoscope 241 to form additional incisions and to permit the placement of additional cannula assemblies through the skin and tissue of the patient and extending into the anatomic space within the patient.

In the event it is desired to utilize a laparoscope 241 of the type hereinbefore described with a guide member 256 which has an opening at the end, the guide member 256 can be formed as shown in FIG. 22 and is provided with a cylindrical recess 257 which is adapted to fit over the distal extremity of the laparoscope 241 and be secured thereto by suitable means such as an adhesive. This guide member 256 can be formed of a suitable material such as metal and is provided with a tapered end 258 that can be formed to provide a knife-life elliptical edge which can be utilized for incising tissue in the manner hereinbefore described with the previous embodiments. Thus, it can be seen that a laparoscope 241 provided with such a guide member 256 can also be utilized for making incisions in the abdominal wall of the patient.

Figure 23:
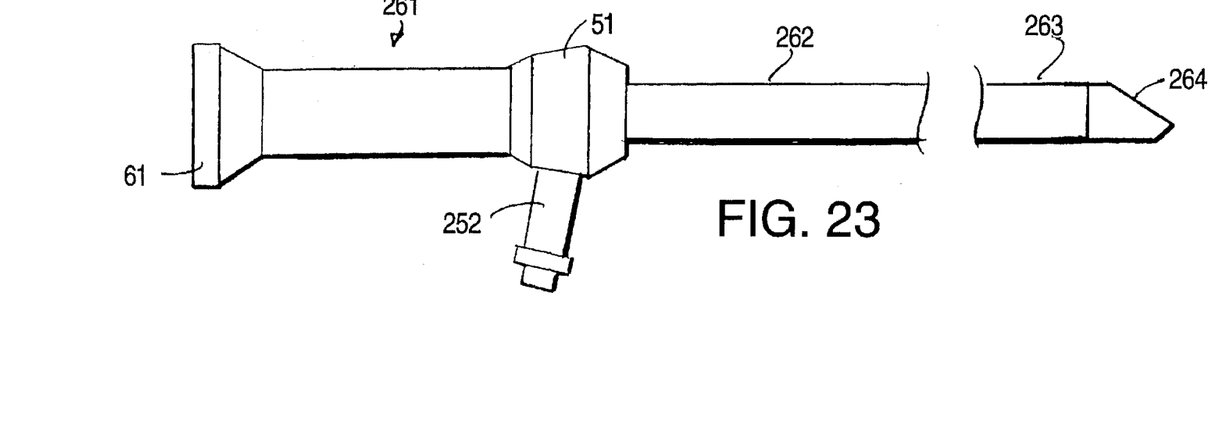
FIG. 23 is a side elevational view of a laparoscope which is provided with a penetrating distal extremity incorporating the salient features of the guide member of the present invention.

In FIG. 23, there is shown a penetrating laparoscope 261 which is similar to the laparoscope 23 hereinbefore described in that it is provided with a body 51 carrying a fitting 252 and having an eyepiece 61. The laparoscope 261 is provide with a cylindrical probe 262 which is very similar to those hereinbefore described with the exception that the distal extremity 263 is provided with an end 264 which can have a conformation very similar to that shown in FIGS. 13, 14 and 15, to permit viewing through the same while utilizing the probe 262 as a guide member for forming an incision from inside an anatomic space to outside the anatomic space. After the distal extremity 263 extends outside the anatomic space, a cannula assembly can be slid over the probe and introduced through the new incision which has been made. The laparoscope 261 then can be withdrawn and utilized to make further incisions from the inside out as desired in connection with the surgical procedure.

It should be appreciated that, if desired, a penetrating laparoscope 261 of the type shown in FIG. 23 can be provided with a telescoping sleeve which can positioned between first and second positions and in the first position presenting a blunt extremity to prevent the incising of tissue and another position being retracted to permit the sharp end 264 to protrude therefrom to permit it to be used for incising operations in the manner hereinbefore described.

In order to make it easier to view the sharp tip of a guide member through a laparoscope inserted into the guide member, the distal extremity of a guide member 266 is shown in FIG. 24. The guide member 266 is tubular in form and has a tapered end 267 with a bore 268 extending therethrough formed by a wall 269. The lower extremity of the wall 269 as viewed in FIG. 24 is canted upwardly and is pinched together to form a sharp point 271. This sharp point 271 because of its position is readily visible through a laparoscope (not shown) positioned in the bore 268. The tapered end 267 is provided with a bevel 272 so that a sharp cutting edge is provided.

Figure 25:
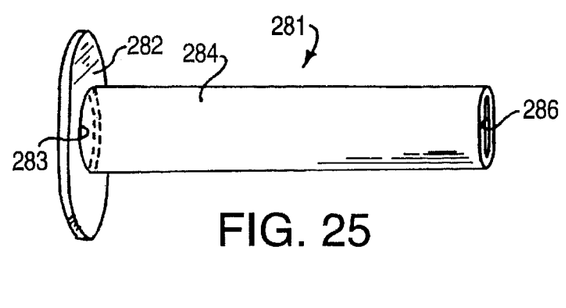
FIG. 25 is an isometric view of an alternative hold down device for use with the guide member shown in FIGS. 1 and 2.

Another embodiment of a hold down device 281 contemplated by the present invention is shown in FIG. 25. This device 281 consists of a circular plate 282 which is provided with a centrally disposed hole 283 therein. A handle 284 is mounted on circular plate 282 and is formed of a cylindrical member which is provided with a bore 286 therein which is of the same size as the hole 283 in the plate 282 and is in registration the hole 283. The cylindrical member forming the handle 284 is of a diameter and length so that it can be readily grasped by the human hand, and thus by way of example can have a length of approximately 4–6 inches and an outside diameter of one inch. The hold down device 281 can be used in a manner similar to the hold down device 71 shown in FIGS. 6 or 8. By having one hand grasp the handle 284, the device 281 can be held so that the hole 283 overlies the skin 92 of the patient where the second incision is to be placed as described in conjunction with the hold down device 71. Thus, it can be seen that the hold down device 281 will protect the surgeon's hand from the knife-like distal extremity of the guide member 22 in the same manner as the hold down device.

From the foregoing it can be seen that there has been provided a relatively simple apparatus with accessory devices and method which greatly facilitate the performance of laparoscopic and other surgical procedures. The apparatus and method particularly facilitate the placement of additional cannula assemblies which are typically used in laparoscopic procedures. With the present apparatus and method it is possible to precisely position the locations of the additional cannula assemblies without injuring other organs or vessels within the body as for example the epigastric artery. The method and apparatus also prevent inadvertent penetration of the peritoneum and other anatomic structures by trocars which are typically used in the placement of additional trocar introducers. The present procedure or method can be carried out with the extraperitoneal space inflated to permit traversal of the distal extremity of the guide member in the extraperitoneal space while carefully viewing its advancement and positioning through the laparoscope. The cannula assemblies have valving therein preventing the escape of the insufflation gases utilized for insufflating the extraperitoneal space.

As also set forth in conjunction with the present invention, it can be seen that the method of the present invention can be utilized with the various embodiments of the apparatus. For example, rather than using a separate guide member, it is possible to utilize attachments for a laparoscope or to fabricate the laparoscope in such manner that it also can be utilized for making incisions from the inside out from an anatomic space.

What is claimed is:

1. A method for making additional incisions in laparoscopic surgery on a patient having a body with tissue and overlying skin with the use of a cannula and a guide member having proximal and distal extremities, comprising:

making a first incision in the skin of the patient overlying a first region in the body of the patient, placing a valved cannula through the first incision into the first region, dissecting the tissue of the body of the patient from the first region to a second region remote from the first region to create an anatomic space, insufflating the anatomic space, introducing the distal extremity of the guide member into the valved cannula, advancing the distal extremity of the guide member into the anatomic space to the second region, and advancing the distal extremity of the guide member in the second region through the skin of the patient from the inside to the outside of the body to provide a second incision so that the distal extremity of the guide member is exposed.

2. A method as in claim 1 further comprising:

inserting a cannula over the exposed distal extremity of the guide member, utilizing the guide member as a guide for the cannula, advancing the cannula over the guide member through the second incision in the body so that the cannula extends into the anatomic space, and removing the distal extremity of the guide member from the cannula.

3. A method as in claim 2 further comprising:

advancing the distal extremity of the guide member to a third region in the anatomic space, advancing the distal extremity of the guide member through the skin of the patient from the inside to the outside of the body to form another incision in a position overlying the third region whereby the distal extremity of the guide member extends outside the body, placing an additional cannula over the distal extremity utilizing the guide member as a guide, advancing the additional cannula through the another incision and into the dissected space, and retracting the guide member from the additional cannula.

4. A method as in claim 2 together with a laparoscope and including inserting the laparoscope into the guide member and observing the advancement of the distal extremity of the guide member in the anatomic space through the laparoscope.

5. A method as in claim 4 further comprising observing the advancement of the distal extremity of the guide member by observing externally of the body of the patient a translucent spot on the skin of the patient created by the laparoscope as the laparoscope in conjunction with the guide member is advanced in the anatomic space to ascertain the position of the distal extremity of the guide member.

6. A method as in claim 2 further including the step of holding down the skin of the patient in the area through which the distal extremity of the guide member is to be advanced through the skin of the patient from the inside to the outside of the anatomic space to a position external of the body of the patient.

7. A method as in claim 6 for use with a hold down device having a hole therein further comprising:

positioning the hold down device so that the hole therein is positioned on the skin of the patient through which the distal extremity of the guide member is to be advanced, and advancing the distal extremity of the guide member through the hole in the hold down device while the hold down device holds down the skin of the patient.

8. A method as in claim 2 wherein the distal extremity of the guide member has a cutting edge and further comprising utilizing the distal extremity of the guide member for making the additional incision in the skin of the patient.

9. A method as in claim 2 together with the step of cutting an incision in the skin of the body of the patient in the second region where the distal extremity of the guide member is to penetrate the skin of the patient from the inside to the outside and thereafter advancing the distal extremity of the guide member through the additional incision.

10. A method for making at least one additional incision through an anatomic wall in surgery on a patient having an anatomic wall overlying a first region in the body of the patient, comprising:

making a first incision through the anatomic wall through the body of the patient, introducing a guide member having a sharp distal extremity through the first incision into the first region, advancing the sharp distal extremity of the guide member to a second region remote from the first region within the body of the patient, and advancing the sharp distal extremity of the guide member through the anatomic wall at the second region so that the sharp distal extremity of the guide member penetrates outwardly from the anatomic wall.

11. A method as in claim 10 together with the step of creating an anatomic space between the first region and the second region by dissecting tissue between the first and second regions.

12. A method as in claim 11 together with the step insufflating the space dissected by the guide member.

13. A method for locating at least one cannula in surgery on a patient having a body with tissue and overlying skin using a guide member having a proximal extremity and a sharp distal extremity, comprising:

introducing the sharp distal extremity of the guide member through the skin of the body through a first incision at a first location within the body, advancing the sharp distal extremity of the guide member in a direction below the skin to a second location remote from the first location, making a second incision in the skin and tissue of the patient at the second location to provide the second distal extremity from within the body to a position outside the body so that the sharp distal extremity of the guide member is exposed outside the body;

placing a cannula over the sharp distal extremity of the guide member exposed outside the body, advancing the cannula through the skin of the patient at the second location utilizing the guide member as a guide, and removing the sharp distal extremity of the guide member from the cannula.

14. A method for locating at least one cannula in surgery on a patient having a body with tissue and overlying skin using a guide member having a proximal extremity and a sharp distal extremity, comprising:

introducing the sharp distal extremity of the guide member through the skin of the body through a first incision at a first location within the body, advancing the sharp distal extremity of the guide member in a direction below the skin to a second location remote from the first location, making a second incision in the skin and tissue of the patient at the second location to provide the second incision at the second location by movement of the sharp distal extremity from within the body to a position outside the body so that the sharp distal extremity of the guide member is exposed outside the body; and withdrawing the distal extremity of the guide member from the second incision and advancing a cannula into the second incision.

15. A method for locating at least one cannula in surgery on a patient having a body with tissue and overlying skin using a guide member having a proximal extremity and a sharp distal extremity, comprising:

introducing the sharp distal extremity of the guide member through the skin of the body through a first incision at a first location within the body, advancing the sharp distal extremity of the guide member in a direction below the skin to a second location remote from the first location, making a second incision in the skin and tissue of the patient at the second location to provide the second incision at the second location by movement of the sharp distal extremity from within the body to a position outside the body so that the sharp distal extremity of the guide member is exposed outside the body;

disposing a laparoscope within the guide member, and viewing by means of the laparoscope the distal extremity of the guide member as it is advanced.

16. A method for locating at least one cannula in surgery on a patient having a body with tissue and overlying skin using a guide member having a proximal extremity and a sharp distal extremity, comprising:

introducing the sharp distal extremity of the guide member through the skin of the body through a first incision at a first location within the body, advancing the sharp distal extremity of the guide member in a direction below the skin to a second location remote from the first location, making a second incision in the skin and tissue of the patient at the second location to provide the second incision at the second location by movement of the sharp distal extremity from within the body to a position outside the body so that the sharp distal extremity of the guide member is exposed outside the body;

causing the guide member to emit light from its distal extremity, and viewing the light from a position exterior of the body to aid in positioning the second incision in the second location.

17. A method for locating at least one cannula in surgery on a patient having a body with tissue and overlying skin using a guide member having a proximal extremity and a sharp distal extremity, comprising:

introducing the sharp distal extremity of the guide member through the skin of the body through a first incision at a first location within the body, advancing the sharp distal extremity of the guide member in a direction below the skin to a second location remote from the first location, making a second incision in the skin and tissue of the patient at the second location to provide the second incision at the second location by movement of the sharp distal extremity from within the body to a position outside the body so that the sharp distal extremity of the guide member is exposed outside the body; and holding down the skin of the patient when the distal extremity of the guide member is advanced from within the body to outside the body.

18. A method for placing cannulae in a body wall of a patient with the use of a guide member having proximal and distal extremities and a channel extending therethrough for endoscopic viewing, comprising:

introducing the distal extremity of the guide member through the body wall at a first incision at a first location;

advancing using endoscopic viewing through the channel the distal extremity of the guide member to a second location remote from the first location;

selecting a particular location to make a second incision from the inside of the body wall to the outside of the body wall at the second location away from any particular anatomic structures in the body wall viewable from inside the body wall by the endoscopic viewing; and advancing the distal extremity of the guide member from the inside of the body wall to the outside of the body wall, thereby making a second incision in the body wall of the patient at the second location avoiding any of the particular anatomic structures.

19. A method as in claim 18 further comprising:

placing a cannula over the distal extremity of the guide member exposed outside the body wall in the second location, advancing the cannula through the second incision in the body wall of the patient at the second location utilizing the guide member as a guide, and removing the distal extremity of the guide member from the cannula.

* * * * *